(12) United States Patent
Kajiyama et al.

(10) Patent No.: US 10,517,570 B2
(45) Date of Patent: Dec. 31, 2019

(54) SWITCH CIRCUIT, ULTRASOUND PROBE USING THE SAME, AND ULTRASONIC DIAGNOSIS APPARATUS

(71) Applicant: HITACHI, LTD., Tokyo (JP)

(72) Inventors: Shinya Kajiyama, Tokyo (JP); Yutaka Igarashi, Tokyo (JP); Toru Yazaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 622 days.

(21) Appl. No.: 15/313,147

(22) PCT Filed: Jun. 13, 2014

(86) PCT No.: PCT/JP2014/065730
§ 371 (c)(1),
(2) Date: Nov. 22, 2016

(87) PCT Pub. No.: WO2015/189982
PCT Pub. Date: Dec. 17, 2015

(65) Prior Publication Data
US 2017/0188996 A1    Jul. 6, 2017

(51) Int. Cl.
*H03K 17/10* (2006.01)
*H03K 17/687* (2006.01)
(Continued)

(52) U.S. Cl.
CPC .............. *A61B 8/4483* (2013.01); *A61B 8/00* (2013.01); *A61B 8/5207* (2013.01);
(Continued)

(58) Field of Classification Search
CPC ........... H03K 2217/0054; H03K 3/012; H03K 2017/066; H03K 17/10; H03K 17/102; H03K 17/687; H03K 17/6871; H03K 17/6874; A61B 8/00; A61B 8/44; A61B 8/4483; A61B 8/4488; A61B 8/4494; A61B 8/52; A61B 8/5208; G01S 7/52017; G01S 7/52079; G01S 7/5208; G01S 7/52082; G01S 7/52084
See application file for complete search history.

(56) References Cited

U.S. PATENT DOCUMENTS 6,759,888 B1    7/2004  Wodnicki
8,834,375 B2    9/2014  Hongou et al.
(Continued)

FOREIGN PATENT DOCUMENTS

JP          62-240032 A    10/1987
JP       2004-274721 A     9/2004
(Continued)

OTHER PUBLICATIONS

International Search Report of PCT/JP2014/065730 dated Aug. 26, 2014.
(Continued)

*Primary Examiner* — Lincoln D Donovan
*Assistant Examiner* — Diana J. Cheng
(74) *Attorney, Agent, or Firm* — Mattingly & Malur, PC

(57) ABSTRACT

A transmit receive switch circuit has a first MOSFET (MN1) and a second MOSFET (MN2), goes into a switch-off state at the time of transmission, and goes into a switch-on state at the time of reception. The first MOSFET (MN1) and the second MOSFET (MN2) are connected between an input terminal (SWIN) and an output terminal (SWOUT). The switch circuit includes a shunt circuit (SHNT) that is connected between a common gate (COMG) and a common source (COMS), the common gate being connected to the gates of the first and second MOSFETs, and the common source being connected to the sources of the first and second MOSFETs. When a signal having a negative voltage relative to a reference voltage is applied to the input terminal, a switch that temporarily turns on causes the shunt circuit to short-circuit the common gate and the common source.

14 Claims, 11 Drawing Sheets

(51) Int. Cl.
*H03K 17/06* (2006.01)
*A61B 8/00* (2006.01)
*G01S 7/52* (2006.01)
*A61B 8/08* (2006.01)
*H03K 3/012* (2006.01)
*G01S 15/89* (2006.01)

(52) U.S. Cl.
CPC .......... *G01S 7/52017* (2013.01); *H03K 3/012* (2013.01); *H03K 17/10* (2013.01); *H03K 17/102* (2013.01); *H03K 17/687* (2013.01); *H03K 17/6874* (2013.01); *G01S 7/5208* (2013.01); *G01S 15/8927* (2013.01); *H03K 2017/066* (2013.01); *H03K 2217/0054* (2013.01)

(56) References Cited

U.S. PATENT DOCUMENTS

| | | | | |
|---|---|---|---|---|
| 8,911,376 | B2* | 12/2014 | Cerofolini | ............. B06B 1/0622 600/437 |
| 2004/0174203 | A1 | 9/2004 | Wodnicki | |
| 2012/0059265 | A1 | 3/2012 | Franchini et al. | |
| 2012/0249210 | A1 | 10/2012 | Shimizu et al. | |
| 2014/0035064 | A1* | 2/2014 | Clark, Jr. | ............ H01L 21/8249 257/378 |
| 2014/0145781 | A1 | 5/2014 | Taylor et al. | |

FOREIGN PATENT DOCUMENTS

| | | | |
|---|---|---|---|
| JP | 2004-363997 | A | 12/2004 |
| JP | 2005-081140 | A | 3/2005 |
| JP | 2006-325044 | A | 11/2006 |
| JP | 2012-152432 | A | 8/2012 |
| JP | 2012-209763 | A | 10/2012 |
| WO | 2011/079880 | A1 | 7/2011 |

OTHER PUBLICATIONS

Extended European Search Report received in corresponding European Application No. 14894656.9 dated Jan. 19, 2018.
Japanese Office Action received in corresponding Japanese Application No. 2016-527591 dated Sep. 18, 2018.

* cited by examiner

SWITCH CIRCUIT, ULTRASOUND PROBE USING THE SAME, AND ULTRASONIC DIAGNOSIS APPARATUS

TECHNICAL FIELD

The present invention relates to a switch circuit, to an ultrasound probe using the switch circuit, and to an ultrasonic diagnosis apparatus. For example, the present invention relates to a transmit receive switch that is used for an ultrasound probe serving as a component of an ultrasonic diagnosis apparatus and is adapted to isolate and protect a receiver circuit formed of a low-voltage device from a high-voltage signal outputted from a transmitter circuit formed of a high-voltage device.

BACKGROUND ART

Ultrasonic diagnosis apparatuses are highly safe medical diagnosis instruments noninvasive to a human body and are smaller in scale than the other medical diagnostic imaging apparatuses such as X-ray diagnosis apparatuses and MRI (Magnetic Resonance Imaging) apparatuses. Further, when a simple procedure is performed to apply an ultrasound probe to a body surface, the ultrasonic diagnosis apparatuses are able to display a real-time image showing the motion of a test object, such as the pulsatory motion of a heart and the movements of a fetus. Consequently, the ultrasonic diagnosis apparatuses are now playing an important role in present-day medicine.

The ultrasonic diagnosis apparatuses transmit ultrasonic waves into a test object when high-voltage drive signals are respectively supplied to multiple transducers built in the ultrasound probe. The multiple transducers respectively receive reflections of the ultrasonic waves, which are generated in accordance with acoustic impedance difference between body tissues in the test object. Based on the reflections of the ultrasonic waves, which are received by the ultrasound probe, the ultrasonic diagnosis apparatuses generate an image.

A transmitter circuit that transmits the high-voltage drive signals to the transducers built in the ultrasound probe is formed of a high-voltage device and capable of generating a high-voltage signal having a peak-to-peak voltage of several tens volts to one hundred and several tens volts. Therefore, when the transmitter circuit is to be implemented as a silicon-based integrated circuit, a large area is required. Meanwhile, the waves reflected from the body tissues in the test object are affected by in vivo attenuation and diffusion. Thus, received signals, which are acoustic-electric converted by the individual transducers, have an extremely small amplitude. A receiver circuit that amplifies such weak signals for signal processing purposes is formed of a low-voltage device in order to deliver low noise performance, low power consumption, and small area.

Each transducer in the ultrasound probe is a transducer in which the same element performs both electric-acoustic conversion and acoustic-electric conversion. The transmitter circuit, which supplies a high voltage, and the receiver circuit, which receives a weak signal, are both connected to the same element. When the transmitter circuit supplies a high-voltage drive signal to a transducer, a switch is normally inserted between the transducer and the receiver circuit in order to electrically protect the receiver circuit formed of a low-voltage device. The switch is called a transmit receive switch.

At the time of transmission, the transmit receive switch is placed in a switch-off state to electrically protect the receiver circuit by separating it from the high-voltage drive signal generated by the transmitter circuit. At the time of reception, the transmit receive switch is placed in a switch-on state to allow a weak signal received from a transducer to pass with low loss. As the transmit receive switch plays the above role, it is necessary that the transmit receive switch have such electrical characteristics as to withstand a high-voltage signal and be formed of a high-voltage device.

Technologies concerning the transmit receive switch are described, for example, in Japanese Unexamined Patent Application Publications No. 2004-363997 (Patent Literature 1) and No. 2004-274721 (Patent Literature 2). A switch circuit described in Patent Literature 1 is configured so that a capacitor is connected between the gate and source of two NMOSFETs, which are basic elements, and adapted to retain a gate-source voltage in order to maintain a switch-on state and a switch-off state. A switch circuit described in Patent Literature 2 is configured so that the gate potentials of two NMOSFETs, which are basic elements, are increased by a PMOSFET to switch on, and that the NMOSFETs short-circuit the gate and the source to switch off.

CITATION LIST

Patent Literature

Patent Literature 1: Japanese Unexamined Patent Application Publication No. 2004-363997
Patent Literature 2: Japanese Unexamined Patent Application Publication No. 2004-274721

SUMMARY OF INVENTION

Technical Problem

As regards the technologies concerning the transmit receive switch, it is significantly necessary for an ultrasound probe that a circuit including the transmit receive switch be implemented within a small area during the use of a high-voltage device having a large area. Thus, it is important that the circuit be formed of a minimum number of high-voltage device elements. In the ultrasound probe, high-voltage signals to be given to the transducers are delayed so as to form and scan an ultrasonic beam. However, the intervals at which the transducers are arranged within the ultrasound probe need to be decreased to the extent that the diffraction-induced influence of a grating lobe is tolerable. Therefore, particularly when a transducer and an integrated circuit including a transmitter/receiver circuit associated with the transducer are superimposed one over the other in a one-to-one dimension, the area of the circuit is limited. Consequently, it is essential that the circuit be disposed in a predetermined area.

Further, it is also necessary that the ultrasound probe deliver low power consumption. The ultrasound probe comes into direct contact with a test object. Therefore, in order to prevent a moderate-temperature burn from being caused by generated heat, the amount of power consumption of a circuit in the ultrasound probe needs to be reduced for adequate heat dissipation.

As described above, a circuit for implementing small-area circuitry within the ultrasound probe with low power consumption is demanded. A small-area transmit receive switch that delivers low power consumption is demanded as a component of the circuit. As the above-described circuit, the switch circuit described in Patent Literature 1 includes two NMOSFETs, which are basic elements, a PMOSFET for invoking the switch-on state, and an NMOSFET for invoking the switch-off state. Area is a problem with the technology described in Patent Literature 1 because four high-voltage MOSFETs, namely, two NMOSFETs, one PMOSFET, and another NMOSFET, are required. Further, the capacitor connected between the gate and source of the two NMOSFETs needs to have a sufficiently great capacitance value in consideration of gradual transition from the switch-on state to the switch-off state or from the switch-off state to the switch-on state. This causes a problem with the area of the capacitor.

Meanwhile, area is also a problem with the technology described in Patent Literature 2 because four high-voltage MOSFETs, namely, two NMOSFETs, one PMOSFET for invoking the switch-on state, and another PMOSFET for invoking the switch-off state, are required. Further, the technology described in Patent Literature 2 requires that a steady-state current continuously flow in a level shift circuit in the switch-off state. This causes a problem in which power is consumed by the steady-state current, which is not used with the technology described in Patent Literature 1.

A typical object of the present invention is to provide a switch circuit that is formed of three high-voltage MOSFETs to achieve small area and is capable of delivering low power consumption without flowing a steady-state current.

The above and other objects and novel features of the present invention will become apparent from the following description and from the accompanying drawings.

Solution to Problem

The following is a brief description of a typical aspect of the invention disclosed in the present application.

A typical switch circuit includes a first MOSFET and a second MOSFET. The first and second MOSFETs are connected between an input terminal and an output terminal. The switch circuit goes into a switch-off state at the time of transmission and goes into a switch-on state at the time of reception. The switch circuit includes a shunt circuit that is connected between a common gate and a common source. The common gate is connected to the gates of the first and second MOSFETs. The common source is connected to the sources of the first and second MOSFETs. When a signal having a negative voltage relative to a reference voltage is applied to the input terminal, a switch that temporarily turns on causes the shunt circuit to short-circuit the common gate and the common source.

More preferably, the shunt circuit includes a filter and a third MOSFET. The filter is connected between the common gate and the common source and formed of a resistor and a capacitor. The third MOSFET is connected to the filter and is used as the switch that short-circuits the common gate and the common source when the voltage between the common gate and the common source increases with a time constant not greater than a time constant equal to the product of the resistance value of the resistor and the capacitance value of the capacitor. The time constant equal to the product of the resistance value of the resistor and the capacitance value of the capacitor is adjustable.

Still more preferably, the switch circuit includes a fifth MOSFET. The fifth MOSFET is connected to the common gate. When turned on, the fifth MOSFET invokes the switch-on state by applying a predetermined supply voltage to the common gate. When turned off, the fifth MOSFET invokes the switch-off state by setting the voltage between the common gate and the common source to a voltage not higher than a threshold voltage.

Advantageous Effect of Invention

An advantageous effect achieved by a typical aspect of the invention disclosed in the present application is briefly described below.

A typical advantageous effect achieved by the present invention is the ability to provide a switch circuit that is formed of three high-voltage MOSFETs to achieve small area and is capable of delivering low power consumption without flowing a steady-state current.

DESCRIPTION OF EMBODIMENTS

Figure 1:
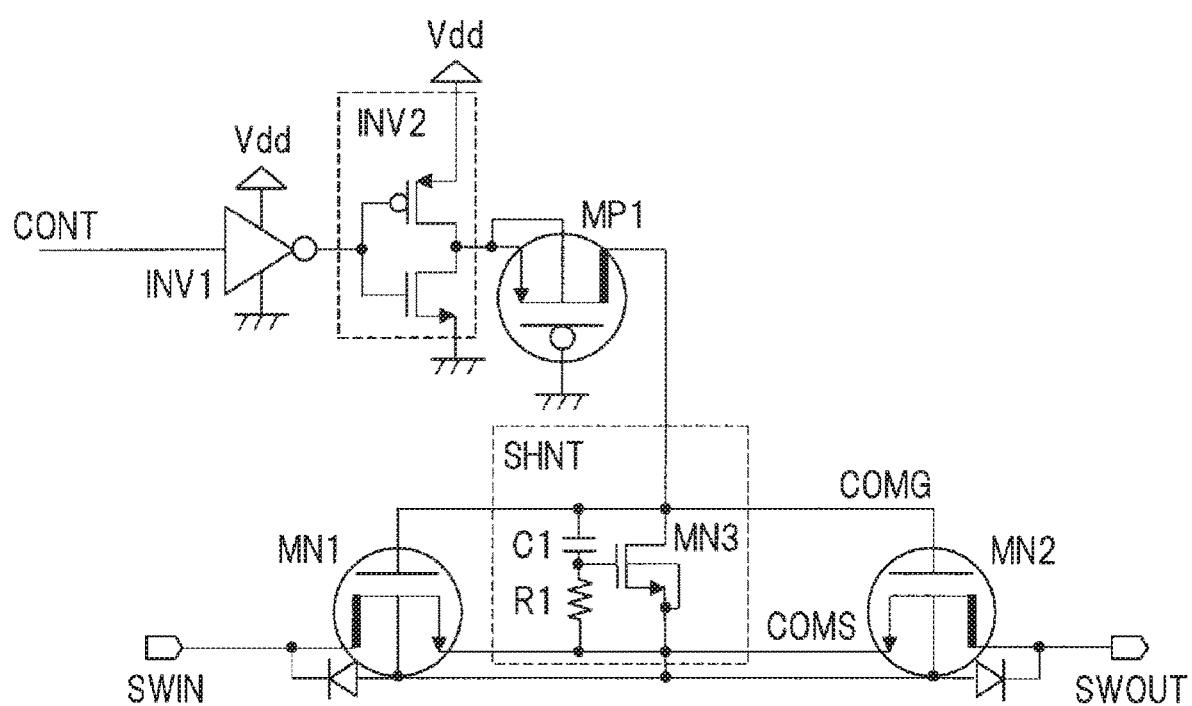
FIG. 1 is a circuit diagram illustrating an exemplary configuration of a transmit receive switch circuit according to a first embodiment of the present invention.

In the following description of the embodiments, if necessary for convenience sake, a description of the present invention will be divided into sections or embodiments, but unless specifically stated, they are not unrelated to each other, but are in such a relation that one is a modification, a detailed explanation, a supplementary explanation, or the like of a part or the whole of the other. Also, in the embodiments described below, when referring to the number of elements (including the number of pieces, numerical values, amounts, ranges, and the like), the number of elements is not limited to a specific number unless specifically stated or except the case where the number of elements is apparently limited to a specific number in principle. The number larger or smaller than the specific number is also applicable.

Further, in the embodiments described below, their components (including element steps and the like) are not always indispensable unless specifically stated or except the case where the components are apparently indispensable in principle. Similarly, in the embodiments described below, when the shapes of the components, the positional relationship between the components, and the like are mentioned, the substantially approximate and similar shapes and the like are included therein unless specifically stated or except the case where it is conceivable that they are apparently excluded in principle. The same goes for the aforementioned numerical values and ranges.

Overview of Embodiments of Present Invention

First of all, embodiments of the present invention will be outlined. When the embodiments of the present invention are outlined, components are designated, for example, by parenthesized reference signs that correspond to those used in the subsequent description of the embodiments.

A typical switch circuit according to the embodiments includes a first MOSFET (MN1) and a second MOSFET (MN2). The first and second MOSFETs are connected between an input terminal (SWIN) and an output terminal (SWOUT). The switch circuit goes into a switch-off state at the time of transmission and goes into a switch-on state at the time of reception. The switch circuit includes a shunt circuit (SHNT) that is connected between a common gate (COMG) and a common source (COMS). The common gate is connected to the gates of the first and second MOSFETs. The common source is connected to the sources of the first and second MOSFETs. When a signal having a negative voltage relative to a reference voltage is applied to the input terminal, a switch that temporarily turns on causes the shunt circuit to short-circuit the common gate and the common source.

More preferably, the shunt circuit includes a filter and a third MOSFET (MN3). The filter is connected between the common gate and the common source and formed of a resistor (R1) and a capacitor (C1). The third MOSFET is connected to the filter and is used as the switch that short-circuits the common gate and the common source when the voltage between the common gate and the common source increases with a time constant not greater than a time constant equal to the product of the resistance value of the resistor and the capacitance value of the capacitor. The time constant equal to the product of the resistance value of the resistor and the capacitance value of the capacitor is adjustable.

Still more preferably, the switch circuit includes a fifth MOSFET (MP1). The fifth MOSFET is connected to the common gate. When turned on, the fifth MOSFET invokes the switch-on state by applying a predetermined supply voltage to the common gate. When turned off, the fifth MOSFET invokes the switch-off state by decreasing the voltage between the common gate and the common source to a voltage not higher than a threshold voltage.

The embodiments based on the above overview of the embodiments of the present invention will now be described in detail with reference to the accompanying drawings. In all the drawings used to describe the embodiments, elements identical with each other are basically designated by the same or associated reference signs and will not be redundantly described.

Further, the embodiments will be described in comparison with comparative technologies with respect to the present invention in order to facilitate the understanding of the present invention. First of all, the comparative technologies with respect to the present invention will be described.

[Comparative Technologies with respect to Present Invention]

Figure 10:
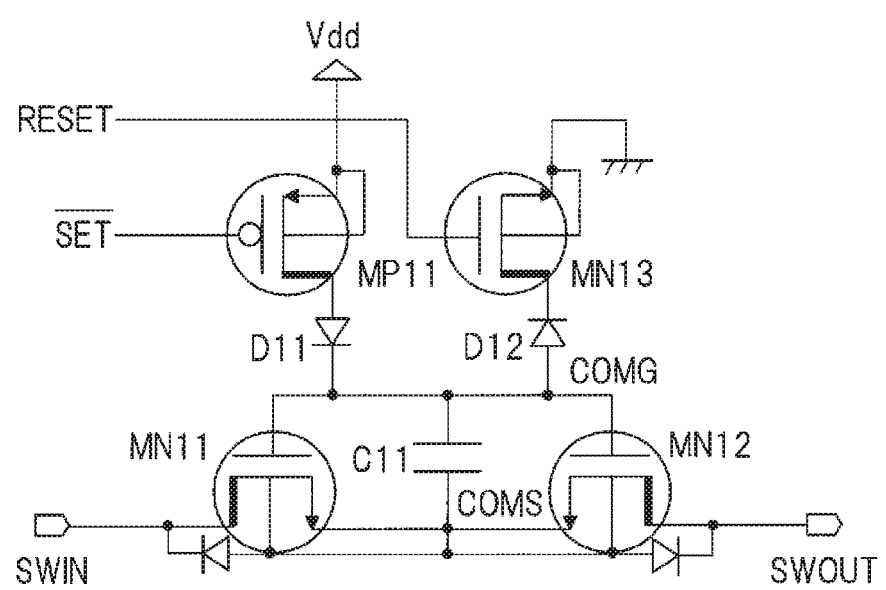
FIG. 10 is a circuit diagram that is obtained by redrawing FIG. 1 in Patent Literature 1 from the viewpoint of the inventors of the present invention in order to illustrate a configuration of the transmit receive switch circuit as a comparative technology with respect to the present invention.
Figure 11:
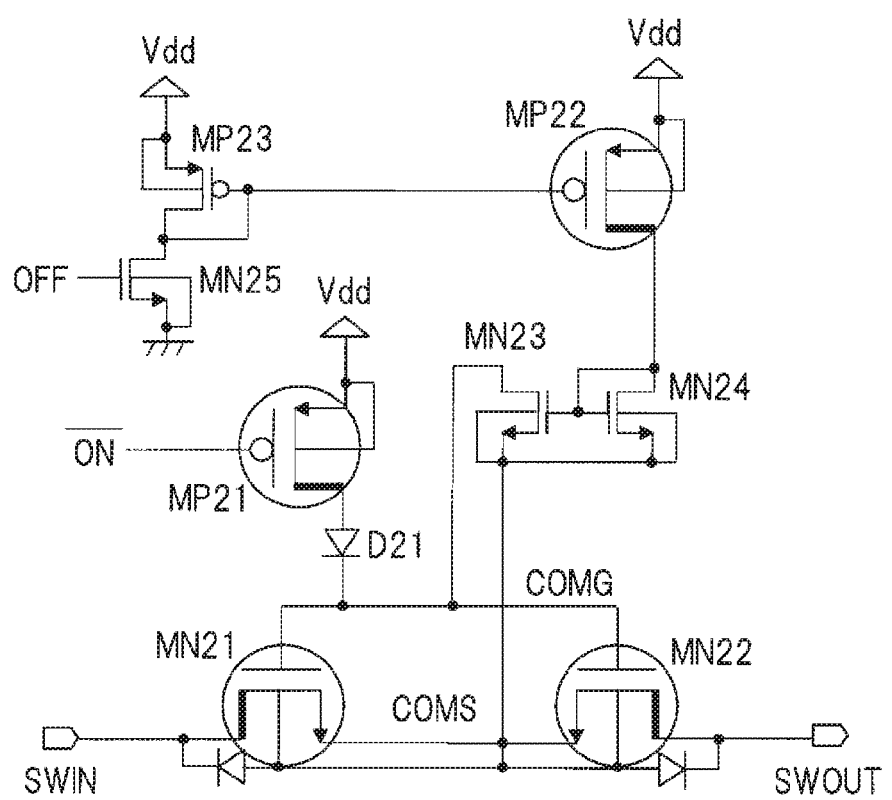
FIG. 11 is a circuit diagram that is obtained by redrawing FIG. 1 in Patent Literature 2 from the viewpoint of the inventors of the present invention in order to illustrate a configuration of the transmit receive switch circuit as a comparative technology with respect to the present invention.

A transmit receive switch circuit according to the comparative technologies with respect to the present invention will now be described with reference to FIGS. 10 and 11. FIG. 10 is a circuit diagram that is obtained by redrawing FIG. 1 in Patent Literature 1 from the viewpoint of the inventors of the present invention in order to illustrate a configuration of the transmit receive switch circuit. FIG. 11 is a circuit diagram that is obtained by redrawing FIG. 1 in Patent Literature 2 from the viewpoint of the inventors of the present invention in order to illustrate a configuration of the transmit receive switch circuit.

FIG. 10 illustrates a switch circuit that corresponds to the contents of FIG. 1 of Patent Literature 1. A transmit receive switch circuit depicted in FIG. 10 includes NMOSFETs (MN11, MN12, MN13), a PMOSFET (MP11), a capacitor C11, and diodes D11, D12. In FIG. 10, the MOSFETs designated by the reference signs MN11, MN12, MN13, and MP11 are encircled. These MOSFETs and subsequently encircled MOSFETs are high-voltage MOSFETs. A basic switch circuit that is formed of two series-connected high-voltage NMOSFETs, namely, the NMOSFET (MN11) and the NMOSFET (MN12), and configured by connecting their gates and connecting their sources is a well-known circuit.

According to Patent Literature 1, the voltage Vgs between a common gate COMG and a common source COMS is retained in the capacitor C11 in order to turn on or off a switch formed of the series-connected NMOSFETs (MN11, MN12). When the switch is to be turned on in a situation where, for example, a switch input SWIN and a switch output SWOUT are connected to a 0-V GND through a resistor, a pulse is applied to a SET signal to turn on the PMOSFET (MP11) and give Vdd—(the forward voltage of the diode D11) to the common gate COMG. The Vdd—(the forward voltage of the diode D11) is then given to the Vgs of the NMOSFETs (MN11, MN12) to turn on the switch. Subsequently, the PMOSFET (MP11) is turned off. The Vgs accumulated in the capacitor C11 as an electrical charge is then retained to maintain the switch-on state.

When the switch-off state is to be invoked, a pulse is applied to a RESET signal of the NMOSFET (MN13) to turn on the NMOSFET (MN13) and reduce the potential of the common gate COMG to a GND level. The Vgs of the NMOSFETs (MN11, MN12) is then set to 0 V. Thus, the switch turns off. Subsequently, the NMOSFET (MN13) turns off so that the Vgs accumulated in the capacitor C11 as an electrical charge is retained to maintain the switch-off state.

The above-described operation is performed by the switch circuit described in Patent Literature 1. The switch circuit consumes charge/discharge power of the capacitor C11 only when the SET signal or the RESET signal makes a transition between the switch-on state and the switch-off state. Further, no steady-state current consumption occurs. Therefore, the switch circuit operates with low power consumption. Meanwhile, the switch circuit uses four high-voltage MOSFETs.

However, according to Patent Literature 1, the capacitor C11 retains the switch-on state and the switch-off state. It is therefore conceivable that an electrical charge may flow into and out of the capacitor C11 due to electrical current leakage through the PMOSFET (MP11), the NMOSFET (MN13), and the diodes D11, D12. If a transition between the switch-on state and the switch-off state is made at long intervals under the above circumstances, the Vgs may vary to make a gradual transition from the switch-on state to the switch-off state or from the switch-off state to the switch-on state. To avoid such a problem, the capacitor C11 should have a sufficiently large capacitance value. Further, when a high-voltage signal is inputted to the switch input SWIN, capacitive voltage division may occur due to large-amplitude variation in the potentials of the common gate COMG and common source COMS even in the switch-off state. To avoid such a problem, the capacitor C11 should have a sufficiently larger capacitance value than the parasitic capacitance values of the common gate COMG and common source COMS. However, when the capacitance value of the capacitor C11 is increased to avoid the above problems, another problem arises with the area of the capacitor C11.

Moreover, the problem with area also arises because four high-voltage MOSFETs are required. An example of a three-element high-voltage MOSFET according to an alternative embodiment is disclosed in FIG. 2 of Patent Literature 2. While the NMOSFET (MN13) in FIG. 10 is eliminated, the three-element high-voltage MOSFET provides the PMOSFET (MP11) with both the SET and RESET functions. If the PMOSFET operates in this instance in order to pass a voltage of 0 V from the source side, a negative voltage needs to be applied to the gate. Thus, a new power supply is required. Even in an embodiment in which the high-voltage MOSFET is formed of three elements, the capacitance value of the capacitor C11 providing against electrical current leakage and voltage division relative to parasitic capacitance is designed in the same manner as for a high-voltage MOSFET formed of four elements. Consequently, there remains a problem with the area of the capacitor C11.

FIG. 11 illustrates a switch circuit that corresponds to the contents of FIG. 1 of Patent Literature 2. A transmit receive switch circuit depicted in FIG. 11 includes NMOSFETs (MN21, MN22, MN23, MN24, MN25), PMOSFETs (MP21, MP22, MP23), and a diode D21.

According to Patent Literature 2, the NMOSFET (MN23) is turned on to short-circuit the common gate COMG and the common source COMS in order to turn off a switch formed of series-connected NMOSFETs (MN21, MN22). When the switch is to be turned on, the NMOSFET (MN25) is turned off, the NMOSFET (MN23) is then turned off without flowing a current to the PMOSFET (MP23), the PMOSFET (MP22), and the NMOSFET (MN24), and the PMOSFET (MP21) is turned on. In this instance, Vdd—(the forward voltage of the diode D21) is given as the voltage Vgs for the NMOSFETs (MN21, MN22) to place the switch in the on state.

When the switch-off state is to be invoked, the PMOSFET (MP21) is turned off, a current mirror is used to flow a current to the NMOSFET (MN25), the PMOSFET (MP23), the PMOSFET (MP22), and the NMOSFET (MN24) in order to let the Vgs of the NMOSFET (MN24) turn on the NMOSFET (MN23). The off state is maintained by allowing the NMOSFET (MN23) to short-circuit the common gate COMG and common source COMS of the NMOSFETs (MN21, MN22). When a high-voltage signal is applied to the switch input SWIN in the switch-off state, large-amplitude variation occurs in the potentials of the common gate COMG and common source COMS even in the switch-off state. Consequently, a level shift circuit formed of the MN25, MP23, MP22, and MN24 is required to maintain the NMOSFET (MN23) in the on state.

The above-described operation is performed by the switch circuit described in Patent Literature 2. The switch circuit is characterized by the NMOSFET (MN23), which short-circuits the common gate COMG and the common source COMS, and the level shift circuit, which turns on the NMOSFET (MN23) to maintain the switch-off state. However, as regards the technology described in Patent Literature 2, there is a problem with area because four high-voltage MOSFETs are required as indicated in FIG. 11, as is the case with the technology described in Patent Literature 1. Further, in order to keep the NMOSFET (MN23) turned on in the switch-off state, it is necessary to continuously flow a steady-state current to the level shift circuit formed of the MN25, the MP23, the MP22, and the MN24. Therefore, there arises another problem as additional power consumption occurs due to the steady-state current unlike in the case of the technology described in Patent Literature 1.

In view of the above circumstances, a switch circuit is required that can be formed of three high-voltage MOSFETs and does not require the flow of a steady-state current. Thus, the embodiments of the present invention provide a switch circuit that is formed of three high-voltage MOSFETs to achieve small area and is capable of delivering low power consumption without flowing a steady-state current. The embodiments of the present invention are described below.

First Embodiment of Present Invention

A transmit receive switch circuit according to a first embodiment of the present invention will now be described with reference to FIGS. 1 to 4.
<Configuration of Transmit Receive Switch Circuit>
FIG. 1 is a circuit diagram illustrating an exemplary configuration of the transmit receive switch circuit according to the first embodiment. Referring to FIG. 1, the transmit receive switch circuit is configured so that a shunt circuit is inserted between a common gate and a common source, and that a high-voltage PMOSFET is used to pull up the common gate.

The transmit receive switch circuit depicted in FIG. 1 includes NMOSFETs (MN1, MN2), a PMOSFET (MP1), logic inverters INV1, INV2, and a shunt circuit SHNT. The shunt circuit SHNT includes a capacitor C1, a resistor R1, and an NMOSFET (MN3). The MN1, the MN2, and the MP1 are high-voltage MOSFETs. The MN3 is a low-voltage MOSFET. A switch input SWIN is an input terminal of the transmit receive switch circuit. A switch output SWOUT is an output terminal of the transmit receive switch circuit.

The NMOSFET (MN1) is connected at the gate to the gate of the NMOSFET (MN2), connected at the source to the source of the NMOSFET (MN2), connected at the drain to the switch input SWIN, and connected at the bulk to the source of the NMOSFET (MN1). The NMOSFET (MN2) is connected at the gate to the gate of the NMOSFET (MN1), connected at the source to the source of the NMOSFET (MN1), connected at the drain to the switch output SWOUT, and connected at the bulk to the source of the NMOSFET (MN2). The NMOSFET (MN1) and the NMOSFET (MN2) form a basic switch configuration in which two high-voltage NMOSFETs are series-connected with their gates interconnected (common gate COMG) and with their sources interconnected (common source COMS).

The PMOSFET (MP1) is connected at the gate to a GND, connected at the source to the output of the logic inverter INV2, connected at the drain to the common gate COMG of the NMOSFET (MN1) and NMOSFET (MN2), and connected at the bulk to the source of the PMOSFET (MP1). The logic inverter INV2 is connected at the input to the output of the logic inverter INV1, and connected at the output to the source of the PMOSFET (MP1). A control signal CONT is inputted to the input of the logic inverter INV1, and the output of the logic inverter INV1 is connected to the input of the logic inverter INV2. The logic inverter INV1 and the logic inverter INV2 are formed by connecting a PMOSFET and an NMOSFET in series as depicted for the logic inverter INV2.

The shunt circuit SHNT includes the capacitor C1, the resistor R1, and the NMOSFET (MN3). The capacitor C1 is connected at one end to the common gate COMG of the NMOSFET (MN1) and NMOSFET (MN2), and connected at the other end to one end of the resistor R1. The resistor R1 is connected at one end to the other end of the capacitor C1, and connected at the other end to the common source COMS of the NMOSFET (MN1) and NMOSFET (MN2). The NMOSFET (MN3) is connected at the gate to a connection point between the capacitor C1 and the resistor R1, connected at the source to the common source COMS of the NMOSFET (MN1) and NMOSFET (MN2), connected at the drain to the common gate COMG, and connected at the bulk to the source of the NMOSFET (MN3).

Referring to FIG. 1, a basic switch circuit that is formed of two series-connected high-voltage NMOSFETs, namely, the NMOSFET (MN1) and the NMOSFET (MN2), and configured by connecting their gates and connecting their sources is a well-known circuit. As for the switch input SWIN and switch output SWOUT depicted in FIG. 1, it is assumed, but not specifically limited to, that the potential is determined externally to FIG. 1, for instance, by connecting to a 0-V GND through a resistor.

The transmit receive switch circuit depicted in FIG. 1 includes the NMOSFETs (MN1, MN2), which are connected between the switch input SWIN and the switch output SWOUT, and goes into the switch-off state at the time of transmission and goes into the switch-on state at the time of reception. In the switch-off state at the time of transmission, the transmit receive switch circuit electrically protects a receiver circuit (a later-described receiver AFE (223) depicted in FIG. 9) by separating it from a high-voltage drive signal generated by a transmitter circuit (a later-described transmitter circuit 221 depicted in FIG. 9). In the switch-on state at the time of reception, the transmit receive switch circuit allows a weak signal received from a transducer (a later-described transducer 21-1 depicted in FIG. 9) to pass to the receiver circuit with low loss.

The shunt circuit SHNT is connected between the common gate COMG and common source COMS of the NMOSFETs (MN1, MN2). When a signal having a negative voltage relative to a reference voltage is applied to the input terminal SWIN, the NMOSFET (MN3) that temporarily turns on causes the shunt circuit SHNT to short-circuit the common gate COMG and the common source COMS.

Specifically, the shunt circuit includes a high-pass filter and the NMOSFET (MN3). The high-pass filter is formed of the resistor R1 and the capacitor C1, which are connected between the common gate COMG and the common source COMS. The NMOSFET (MN3) is connected to the high-pass filter. The NMOSFET (MN3) short-circuits the common gate COMG and the common source COMS when the voltage between the common gate COMG and the common source COMS increases with a time constant not greater than a time constant equal to the product of the resistance value of the resistor R1 and the capacitance value of the capacitor C1. The time constant equal to the product of the resistance value of the resistor R1 and the capacitance value of the capacitor C1 is adjustable.

The PMOSFET (MP1) is used to pull up a common gate potential and is connected to the common gate COMG. When turned on, the PMOSFET (MP1) invokes the switch-on state by applying a predetermined supply voltage to the common gate COMG. When turned off, the PMOSFET (MP1) invokes the switch-off state by applying a voltage not higher than a threshold voltage of the PMOSFET (MP1) between the common gate COMG and the common source COMS. Specifically, the PMOSFET (MP1) is connected to the logic inverters INV1, INV2 to which a logical high or logical low control signal CONT is inputted. Consequently, when a transition is made between the switch-on state and the switch-off state, the logic inverters INV1, INV2 supply a charge/discharge current for the common gate COMG through the PMOSFET (MP1). The control signal CONT to be inputted to the logic inverter INV1 is supplied from a later-described subarray control logic circuit 24 depicted in FIG. 9.

Figure 4:
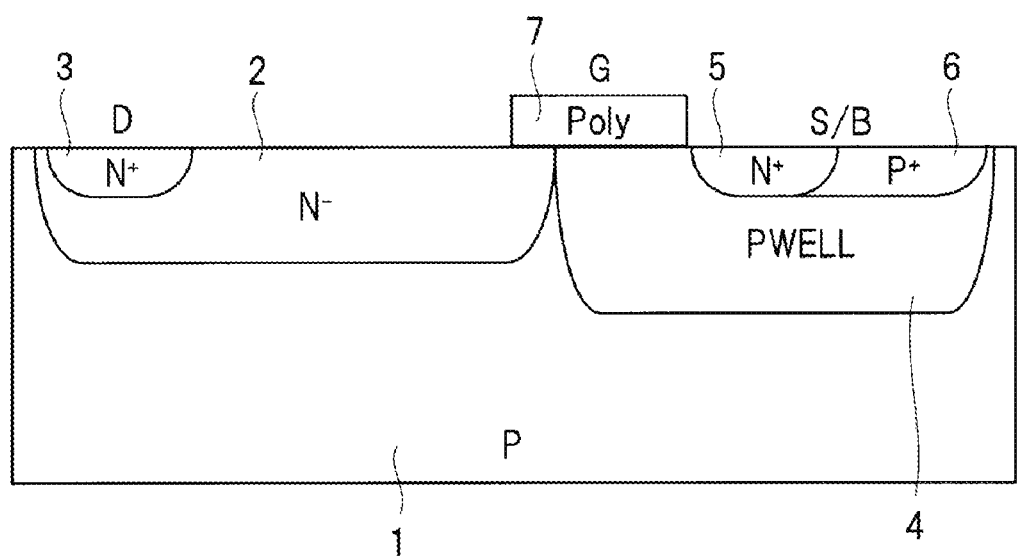
FIG. 4 is a cross-sectional view illustrating a common structure of a high-voltage MOSFET that is included in the transmit receive switch circuit configured as illustrated in FIG. 1.

The NMOSFETs (MN1, MN2) and the PMOSFET (MP1), which are encircled in FIG. 1, are high-voltage MOSFETs. The high-voltage MOSFETs generally use an LDMOS (Laterally Diffused MOS) device illustrated in FIG. 4. FIG. 4 is a cross-sectional view illustrating a common structure of a high-voltage MOSFET (the description of the cross-section is omitted). In the LDMOS depicted in FIG. 4, a drain D is formed by an N+ layer 3, which is formed in an N− layer 2 over a P-type substrate 1, and a source S and a bulk B are respectively formed by an N+ layer 5 and a P+ layer 6, which are formed in a PWELL layer 4 over the P-type substrate 1. A gate G is formed by a Poly (polysilicon) layer 7, which is formed over the surface of the PWELL layer 4 and N layer 2.

The LDMOS is a device structured to reduce the electric field strength between the drain D and the gate G. An extremely large area is required to provide a drift region between the drain D and the gate G. The LDMOS is structured so that the source S and the drain D are asymmetric, and that the source S is connected to the bulk B. The structure between the drain D and the gate G and the structure between the drain D and the source S withstand a voltage higher than several tens of volts or 100 volts. However, only a low voltage, such as 5 volts, can be applied between the gate G and the source S. Referring to FIG. 1, for example, the line drawn to the left of a symbol indicative of the NMOSFET (MN1) is thickened. It signifies that the left side is structured to form a drain where the drift region for reducing the electric field exists. The diode between the bulk B and drain D of the NMOSFETs (MN1, MN2) is a parasitic diode formed of a high-voltage NMOSFET.

<Operation of Transmit Receive Switch Circuit>

Figure 2:
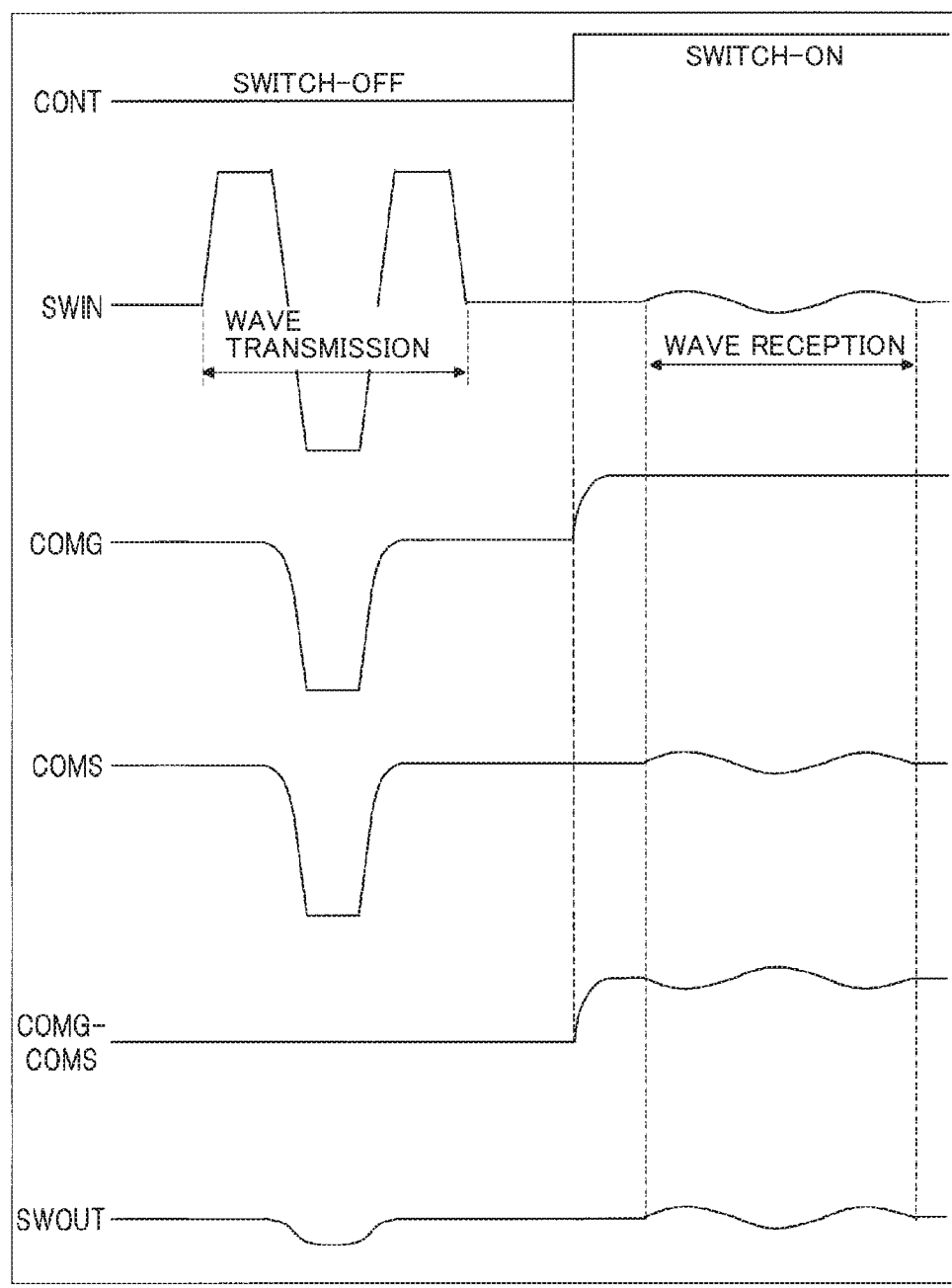
FIG. 2 is a timing diagram illustrating an example of an operation that is performed when the transmit receive switch circuit is configured as illustrated in FIG. 1.

FIG. 2 is a timing diagram illustrating an example of an operation that is performed when the transmit receive switch circuit is configured as illustrated in FIG. 1. FIG. 2 illustrates the transmission of a wave carrying a high-voltage signal during a switch-off period and the reception of a wave carrying a weak signal during a switch-on period.

When the control signal CONT depicted in FIG. 1 is at a logical low level, it is assumed that the PMOSFET (MP1), which is a high-voltage MOSFET for common gate potential pull-up, is off, and that a switch series-connected to the NMOSFETs (MN1, MN2) is off as the voltage Vgs between the common gate COMG and the common source COMS is not higher than a threshold voltage. When a high-voltage signal from the transmitter circuit drives the transducer in the switch-off state as indicated in FIG. 2, the high-voltage signal is inputted to the switch input SWIN in the form of a transmitted wave depicted in FIG. 2. The transmitted wave has a waveform that changes from a reference voltage (the center voltage of a signal: 0 V) through a positive voltage, a negative voltage, the positive voltage to the reference voltage at a predetermined slew rate (gradient: $\Delta V/\Delta t$). When, in this instance, the switch input SWIN is driven by the negative voltage, the structural drain of the NMOSFET (MN1) depicted in FIG. 1 is driven by the negative voltage. Thus, the structural drain electrically acts as a temporary source so that the NMOSFET (MN1) turns on very shallowly. Consequently, the voltage of the common source COMS decreases to the negative voltage in accordance with the switch input SWIN as indicated by a waveform in FIG. 2.

Referring now to FIG. 1, the NMOSFET (MN3), which forms the shunt circuit SHNT, is inserted between the common gate COMG and the common source COMS, and no high voltage can be applied between them. Therefore, the NMOSFET (MN3) may be a low-voltage NMOSFET. Under normal conditions, the NMOSFET (MN3) is off because its gate is connected to its source through the resistor R1. When the switch input SWIN is driven by the negative voltage during a wave transmission period depicted in FIG. 2 so that the voltage of the common source COMS changes toward the negative voltage, the voltage of the common gate COMG in a floating state attempts to decrease with a delay. Therefore, the voltage between the common gate COMG and the common source COMS increases in accordance with a wave transmission slew rate. In this instance, the impedance of the capacitor C1 included in the shunt circuit SHNT decreases. Therefore, the voltage of the common gate COMG is transmitted to the gate of the NMOSFET (MN3) to temporarily turn on the NMOSFET (MN3). That is to say, the capacitor C1 and the resistor R1, which are included in the shunt circuit SHNT, form an incomplete differentiation circuit, that is, a high-pass filter.

Consequently, when a negative voltage wave is transmitted to increase the voltage between the common gate COMG and the common source COMS at a slew rate not higher than an RC time constant that depends on the capacitor C1 and the resistor R1, such a change is transmitted to the gate of the NMOSFET (MN3). Thus, each time a negative voltage wave is transmitted, the NMOSFET (MN3) turns on to short-circuit the common gate COMG and the common source COMS and maintain the switch-off state of the NMOSFETs (MN1, MN2) depicted in FIG. 1. Therefore, the presently described first embodiment does not require the level shift circuit described in Patent Literature 2, which maintains the NMOSFET (MN3) in the on state at the time of transmission in the switch-off state, and does not flow a steady-state current. As a result, no steady-state power consumption occurs.

The role played by the capacitor C1 included in the shunt circuit SHNT depicted in FIG. 1 is different from the role played by a voltage retention capacitor disposed between the common gate COMG and the common source COMS as described in Patent Literature 1. More specifically, the capacitor C1 forms a high-pass filter. Therefore, a required RC time constant should be determined in accordance with a wave transmission frequency while both the capacitor C1 and the resistor R1 are taken into consideration. Characteristics are consistently determined by the product of PC. When a great resistance value is used, a small capacitance value may be used. Consequently, a large area mentioned in Patent Literature 1 is not required.

The floating state of the common gate COMG depicted in FIG. 1 will now be described in comparison with Patent Literature 1. According to Patent Literature 1, the common gate COMG depicted in FIG. 10 is in the floating state in the switch-on state and in the switch-off state. In this instance, what are feared are an off-leak current of the PMOSFET (MP11) and NMOSFET (MN13) in FIG. 10, Vgs variation due to inflow to and outflow from the capacitor C1, and a transition from the switch-on state to the switch-off state or from the switch-off state to the switch-on state.

Meanwhile, according to the first embodiment, the NMOSFET (MN3) in the shunt circuit SHNT depicted in FIG. 1 is off when no wave is transmitted at the time of transmission, that is, in the switch-off state. Therefore, the common gate COMG is in the floating state. In this instance, although the PMOSFET (MP1) in FIG. 1 is off, the gate of the PMOSFET (MP1) is at 0 V, its source is at 0 V, its drain, that is, the common gate COMG of the NMOSFETs (MN1, MN2) is floating at 0 V while no wave is transmitted, and all terminals of the PMOSFET (MP1) are at 0 V. Thus, no off-leak current flows to the PMOSFET (MP1). As described above, the common gate COMG according to the first embodiment, which is depicted in FIG. 1, is floating when not wave is transmitted in the switch-off state. However, a leak current passed through the PMOSFET (MP1) does not invoke the switch-on state by charging the parasitic capacitance of the common gate COMG. Further, when a negative voltage wave is transmitted, the shunt circuit SHNT operates to temporarily turn on the NMOSFET (MN3) and guarantee the switch-off state. Consequently, no considerable fear arises due to the fact that the common gate COMG is floating.

The switch-on state at the time of reception will now be described. When a logical high level is inputted to the control signal CONT in FIG. 1, the voltage at the source of the PMOSFET (MP1) increases to a supply voltage Vdd. The PMOSFET (MP1) then turns on so that the common gate COMG is pulled up to Vdd. Vdd is then applied between the common gate COMG and the common source COMS as Vgs to turn on the NMOSFET (MN1) and the NMOSFET (MN2). This invokes the switch-on state. In the switch-on state, a received signal passes from the switch input SWIN to the switch output SWOUT as indicated in FIG. 2. In the switch-on state, no steady-state power consumption occurs because the shunt circuit SHNT does not operate, the NMOSFET (MN3) in FIG. 1 remains off, and no steady-state current flows.

Further, when on-off control is exercised over the PMOSFET (MP1) in FIG. 1 in order to switch between the switch-on state and the switch-off state, it is preferable that the source of the PMOSFET (MP1) be controlled instead of the gate. If the gate is used to exercise on-off control, a transient current flows from Vdd through the PMOSFET (MP1) when a transition is made from the switch-off state to the switch-on state. The parasitic capacitance of the common gate COMG is then charged to increase the potential of the common gate COMG. However, when a transition is made from the switch-on state to the switch-off state, there is no path for discharging the electrical charge at the common gate COMG. Therefore, the electrical charge stored in the parasitic capacitance of the common gate COMG is discharged only by an off-leak current of the NMOSFET (MN3) in the shunt circuit SHNT. Thus, a very long time is required for the transition from the switch-on state to the switch-off state.

Meanwhile, when the source of the PMOSFET (MP1) in FIG. 1 is controlled, the electrical charge stored in the parasitic capacitance of the common gate COMG can be discharged to a 0-V GND through the PMOSFET (MP1) and the NMOSFET in the logic inverter INV2. When the source potential of the PMOSFET (MP1) decreases from Vdd to a 0-V GND level during the transition from the switch-on state to the switch-off state, the voltage Vgs between the gate and source of the PMOSFET (MP1) shallows. When the voltage Vgs shallows to reach the threshold voltage of the PMOSFET (MP1), the PMOSFET (MP1) turns off. If, for example, the threshold voltage of the PMOSFET (MP1) is −1 V, the potential of the common gate COMG in the circuit configuration illustrated in FIG. 1 can be decreased to 1 V. If the threshold voltages of the NMOSFET (MN1) and NMOSFET (MN2) are similarly 1 V, the transmit receive switch circuit can be placed in the switch-off state. When a negative voltage wave is transmitted to cause the shunt circuit SHNT to short-circuit the common gate COMG and the common source COMS, the Vgs can be set to 0 V.

<Operation Performed with Shunt Circuit Eliminated>

Figure 3:
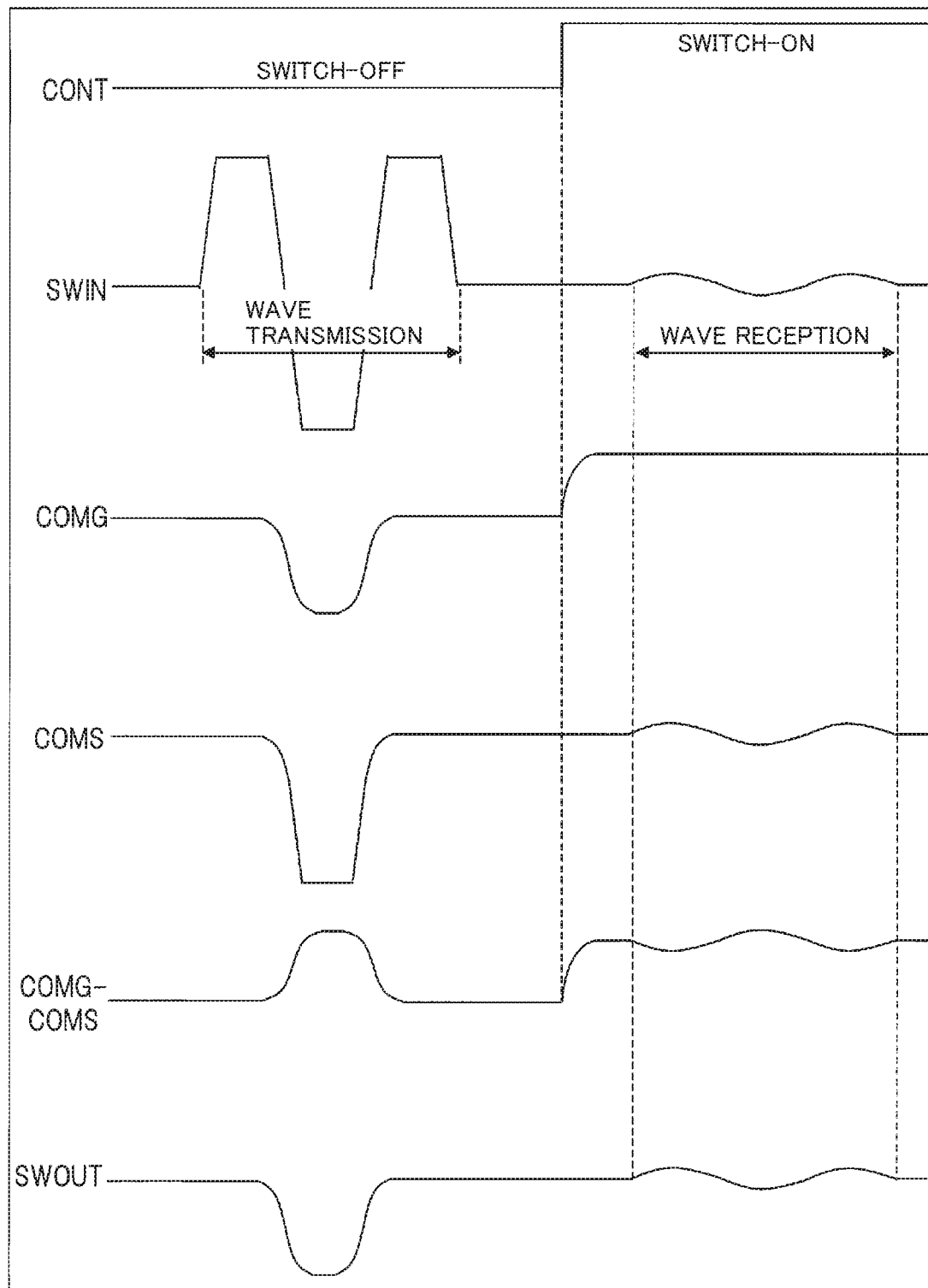
FIG. 3 is a timing diagram illustrating an example of an operation that is performed when a shunt circuit is eliminated from the transmit receive switch circuit configured as illustrated in FIG. 1.

FIG. 3 is a timing diagram illustrating an example of an operation that is performed when the shunt circuit SHNT is eliminated from the transmit receive switch circuit configured as illustrated in FIG. 1. In order to make a supplementary explanation of the role of the shunt circuit SHNT in the first embodiment, FIG. 3 depicts waveforms obtained when the shunt circuit SHNT does not exist in the circuit depicted in FIG. 1.

At the time of transmission, the shunt circuit SHNT does not short-circuit the common gate COMG and the common source COMS even when a negative voltage wave is transmitted in the switch-off state. Therefore, the common gate COMG remains in the floating state. If, in this instance, a large-capacity capacitor for retaining Vgs is disposed between the common gate COMG and the common source COMS as described in Patent Literature 1, the switch-off state can be maintained. However, the switch-off state cannot be maintained by parasitic capacitance alone. Thus, as indicated in FIG. 3, the switch is temporarily placed in the on state at the time of wave transmission. If the switch-on state temporarily prevails, a negative voltage having a large amplitude is outputted to the switch output SWOUT. This may cause a low-voltage receiver circuit to become faulty. In the first embodiment, the shunt circuit SHNT depicted in FIG. 1 guarantees the switch-off state without a large-capacity capacitor for retaining Vgs as described in Patent Literature 1 and allows high-voltage MOSFETs to operate a three-element operation without consuming a steady-state current.

Advantageous Effects of First Embodiment

The transmit receive switch circuit according to the first embodiment, which has been described above, achieves small area by including three high-voltage MOSFETs, namely, the NMOSFETs (MN1, MN2) and the PMOSFET (MP1), and uses the shunt circuit SHNT to deliver low power consumption without flowing a steady-state current. That is to say, the first embodiment provides the transmit receive switch circuit having a small area with low power consumption as at the time of transmission, the transmit receive switch circuit goes into the switch-off state and electrically protects the receiver circuit by separating it from a high-voltage drive signal generated by the transmitter circuit; and at the time of reception, the transmit receive switch circuit goes into the switch-on state and allows a weak signal received from the transducer to pass with low loss. More specifically, the following advantageous effects can also be obtained.

(1) The transmit receive switch circuit includes the shunt circuit SHNT, which is connected between the common gate COMG and the common source COMS. Therefore, when a negative-voltage signal is applied to the switch input SWIN, the shunt circuit SHNT temporarily short-circuits the common gate COMG and the common source COMS. This makes it possible to guarantee the off state of the switch circuit.

(2) The shunt circuit SHNT includes a high-pass filter that is formed of the resistor R1 and the capacitor C1. Therefore, when a time constant equal to the product of the resistance value of the resistor R1 and the capacitance value of the capacitor C1 is adjusted, the shunt circuit SHNT can arbitrarily adjust a time constant for short-circuiting in accordance with a change in the voltage between the common gate COMG and the common source COMS that is not greater than the former time constant.

(3) The transmit receive switch circuit includes the PMOSFET (MP1), which is connected to the common gate COMG. Therefore, the switch-on state can be invoked by turning on the PMOSFET (MP1), connecting the common gate COMG to a predetermined supply voltage through the PMOSFET (MP1), and applying the predetermined supply voltage to the common gate COMG. Further, the switch-off state can be invoked by turning off the PMOSFET (MP1) to decrease the voltage between the common gate COMG and the common source COMS to a level not higher than the threshold voltage of the PMOSFET (MP1).

(4) The transmit receive switch circuit includes the logic inverters INV1, INV2, which controls the source of the PMOSFET (MP1) in accordance with the logical high or logical low control signal CONT. Therefore, when a transition is made between the switch-on state and the switch-off state, the logic inverters INV1, INV2 can supply the charge/discharge current for the common gate COMG through the PMOSFET (MP1).

Second Embodiment of Present Invention

Figure 5:
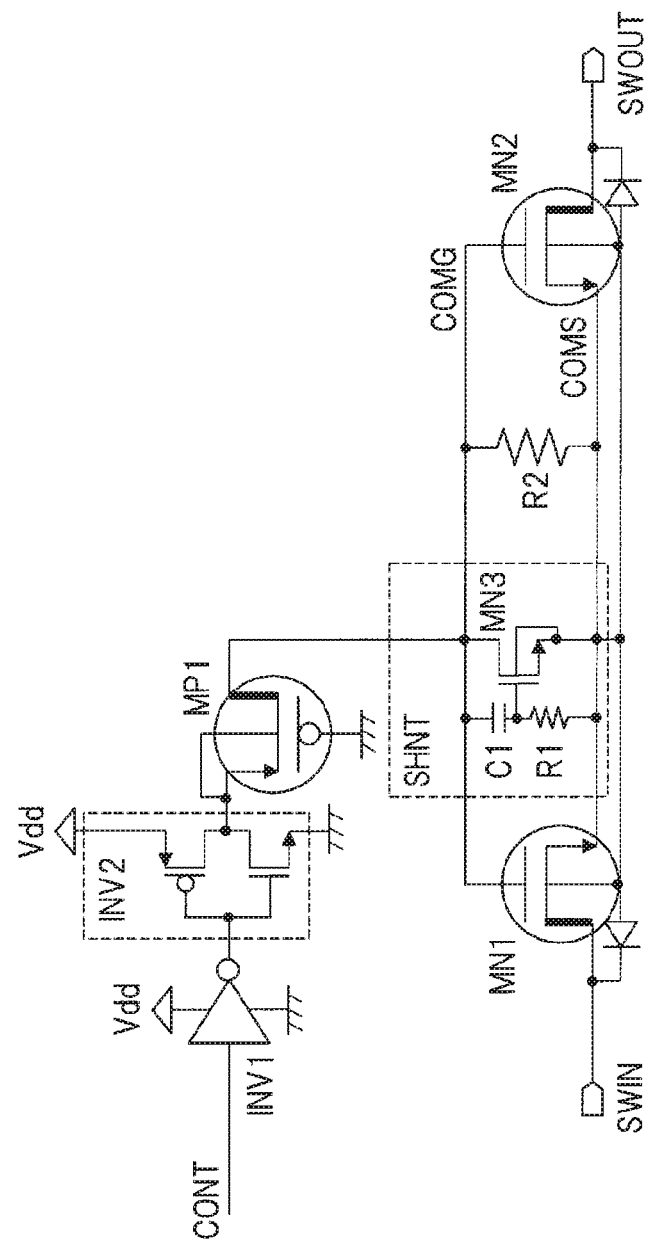
FIG. 5 is a circuit diagram illustrating an exemplary configuration of the transmit receive switch circuit according to a second embodiment of the present invention.

The transmit receive switch circuit according to a second embodiment of the present invention will now be described with reference to FIG. 5. FIG. 5 is a circuit diagram illustrating an exemplary configuration of the transmit receive switch circuit according to the second embodiment. Referring to FIG. 5, the transmit receive switch circuit is configured by inserting a resistor between the common gate and the common source in order to reduce the influence of an unintended transition from the switch-off state to the switch-on state, which may be caused by the floating of the common gate and a leak current. The second embodiment will be described mainly by explaining about its difference from the first embodiment, which has been described earlier.

According to the first embodiment, which is depicted in FIG. 1, the common gate COMG is in the floating state while no wave is transmitted at the time of transmission, that is, during the switch-off state. As far as the switch input SWIN and switch output SWOUT in FIG. 1 are connected to a 0-V GND through a resistor outside the circuit, the potentials of the terminals of the PMOSFET (MP1) in FIG. 1 are all 0 V. Therefore, the Vgs between the common gate COMG and the common source COMS will not possibly be varied by an off-leak current of the PMOSFET (MP1). As for a circuit that uses a high voltage, however, an unintended inversion layer may be formed over a substrate having a high-voltage wiring. It is therefore feared that a leak current may flow when a high voltage is applied to an interlayer film or an element isolation region.

In view of the above circumstances, the second embodiment is configured so that a resistor R2 depicted in FIG. 5 is inserted between the common gate COMG and the common source COMS. Therefore, the floating of the common gate COMG as viewed from the common source COMS can be avoided in the switch-off state, and thus the transition from the switch-off state to the switch-on state can be prevented from being made by a leak current caused by the aforementioned high voltage. That is to say, the switch-off state can be guaranteed by preventing the switch-on state from being invoked by a change in the voltage of the common gate COMG due to parasitic capacitance charge/discharge caused by a leak current.

However, as the resistor R2 is inserted, a Vdd/R2 steady-state current flows at the time of reception, that is, in the switch-on state. When the resistance value of the resistor R2 is small, the resistance to current leakage can be increased. In such an instance, however, the steady-state current also increases to increase the power consumption.

In view of the above circumstances, the second embodiment selects a resistance value that is high enough to suppress the influence of current leakage. Consequently, the influence exerted by the floating of the common gate COMG can be reduced while suppressing an increase in the power consumption.

Unlike the transmit receive switch circuit according to the first embodiment, the above-described transmit receive switch circuit according to the second embodiment can reduce the influence of an unintended transition from the switch-off state to the switch-on state, which may be caused by the floating of the common gate COMG and a leak current. Thus, an increase in the power consumption can be suppressed.

Third Embodiment of Present Invention

Figure 6:
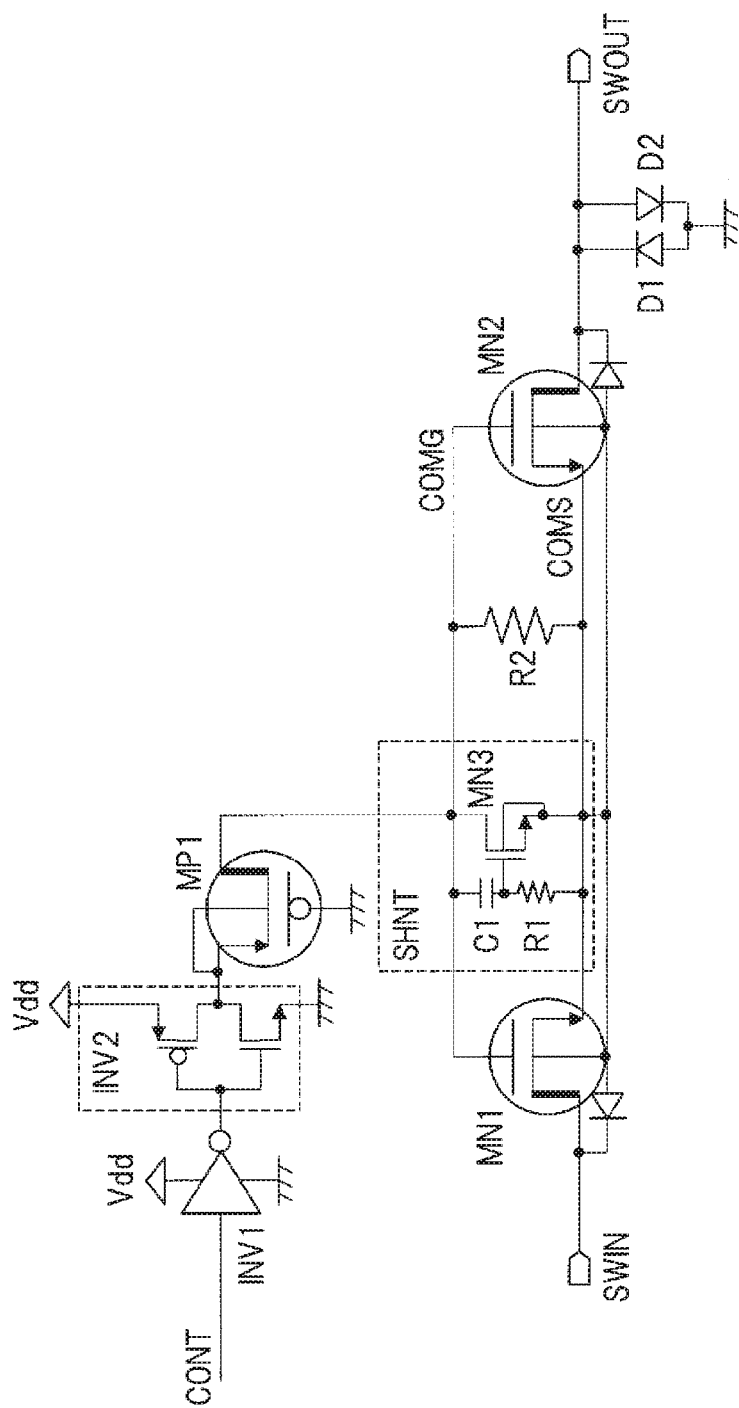
FIG. 6 is a circuit diagram illustrating an exemplary configuration of the transmit receive switch circuit according to a third embodiment of the present invention.

The transmit receive switch circuit according to a third embodiment of the present invention will now be described with reference to FIG. 6. FIG. 6 is a circuit diagram illustrating an exemplary configuration of the transmit receive switch circuit according to the third embodiment. Referring to FIG. 6, the transmit receive switch circuit is configured to improve transmit/receive isolation performance by providing clamp diodes for the output of the transmit receive switch circuit. The third embodiment will be described mainly by explaining about its difference from the first and second embodiments, which have been described earlier.

For example, according to the second embodiment, which is depicted in FIG. 5, the parasitic capacitance of each device causes coupling between the switch input SWIN and the switch output SWOUT. Thus, a high-frequency component of a high-voltage signal passes through. Particularly when the gate widths of the NMOSFETs (MN1, MN2) are increased to decrease the on-resistance of the transmit receive switch circuit, the high-voltage MOSFETs increase in size. This increases the gate-source parasitic capacitance, the gate-drain parasitic capacitance, and the drain-source parasitic capacitance, thereby degrading the transmit/receive isolation performance. It is therefore feared that a low-voltage receiver circuit connected to the switch output SWOUT may become faulty.

In view of the above circumstances, the third embodiment is configured so that a signal line of the switch output SWOUT is connected to the cathode of a diode D1 and to the anode of a diode D2 as depicted in FIG. 6. Further, the anode of the diode D1 and the cathode of the diode D2 are connected to the GND. As the switch output SWOUT is connected to the diode D1 and the diode D2, the diodes D1, D2 clamp high- and low-potential sides with respect to 0 V, which is the center of a signal at the time of reception. This allows a weak signal to pass at the 0-V center at the time of reception, and protects the receive circuit at the time of transmission by providing parasitic capacitance coupling to limit the amplitude of a passed high-frequency component.

Unlike the transmit receive switch circuit according to the first or second embodiment, the above-described transmit receive switch circuit according to the third embodiment can improve the transmit/receive isolation performance by allowing a weak signal to pass at the 0-V center at the time of reception and protecting the receive circuit at the time of transmission.

It should be noted that the third embodiment can be implemented without connecting the resistor R2, which is characteristic of the second embodiment as described earlier. That is to say, the advantageous effects of the third embodiment can be obtained even when the resistor R2 is eliminated from the configuration illustrated in FIG. 6.

Fourth Embodiment of Present Invention

Figure 7:
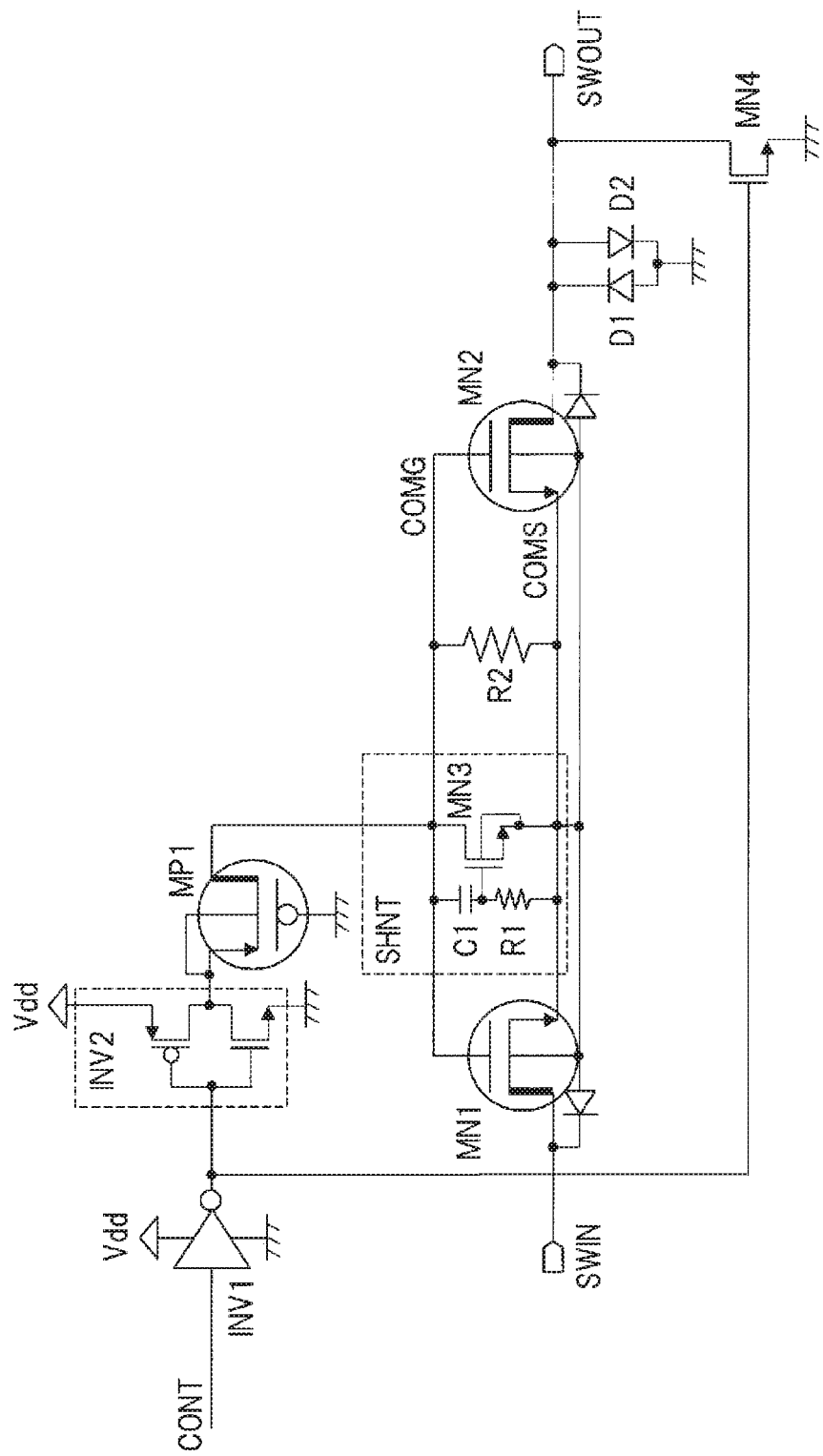
FIG. 7 is a circuit diagram illustrating an exemplary configuration of the transmit receive switch circuit according to a fourth embodiment of the present invention.

The transmit receive switch circuit according to a fourth embodiment of the present invention will now be described with reference to FIG. 7. FIG. 7 is a circuit diagram illustrating an exemplary configuration of the transmit receive switch circuit according to the fourth embodiment. Referring to FIG. 7, the transmit receive switch circuit is configured to improve the transmit/receive isolation performance by incorporating a switch that short-circuits the output of the transmit receive switch circuit to the GND. The fourth embodiment will be described mainly by explaining about its difference from the first to third embodiments, which have been described earlier.

In the fourth embodiment, a switch formed of an NMOSFET (MN4) is connected to the switch output SWOUT. The NMOSFET (MN4) is a low-voltage MOSFET. The NMOSFET (MN4) is connected at the drain to a signal line of the switch output SWOUT and connected at the source to the GND. Further, the NMOSFET (MN4) is connected at the gate to the output of the logic inverter INV1 and is controlled by a signal outputted from the logic inverter INV1. As the NMOSFET (MN4) is connected to the switch output SWOUT, the transmit/receive isolation performance is improved by turning on the switch formed of the NMOSFET (MN4) in the switch-off state. The NMOSFET (MN4) connects the switch output SWOUT to 0 V with low on-resistance, and suppresses changes in the switch output SWOUT that are caused by a high-frequency component passed due to parasitic capacitance coupling. In the switch-on state, the NMOSFET (MN4) is turned off to pass a received signal.

Unlike the transmit receive switch circuit according to the first, second, or third embodiment, the above-described transmit receive switch circuit according to the fourth embodiment can improve the transmit/receive isolation performance in the switch-off state.

It should be noted that the fourth embodiment can be implemented without connecting the resistor R2, which is characteristic of the second embodiment as described earlier, or without connecting the diodes D1, D2, which are characteristic of the third embodiment as described earlier. That is to say, the advantageous effects of the fourth embodiment can be obtained even when the resistor R2 is eliminated from the configuration illustrated in FIG. 7 or when the diodes D1, D2 are eliminated from the configuration illustrated in FIG. 7.

Fifth Embodiment of Present Invention

Figure 8:
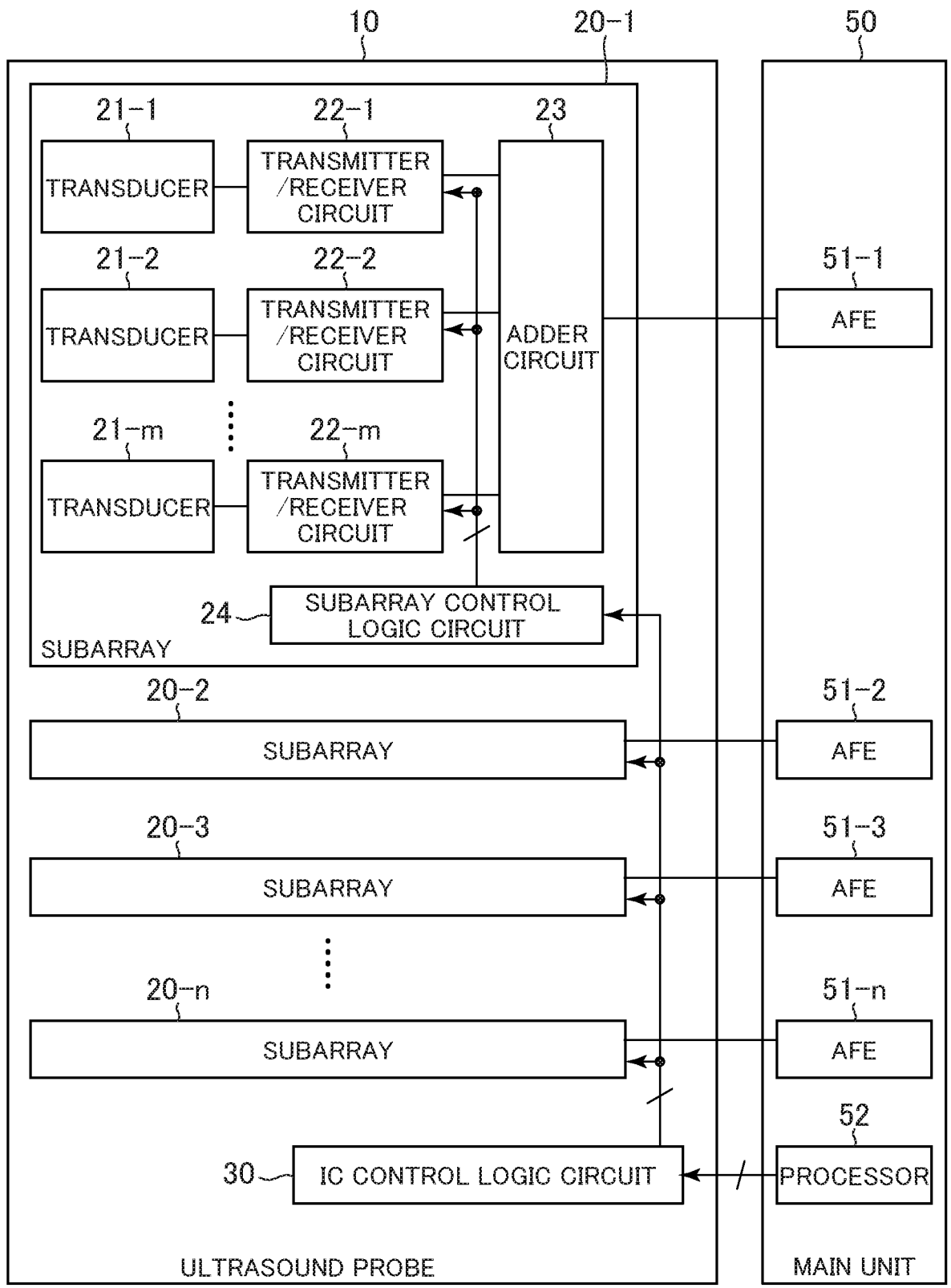
FIG. 8 is a block diagram illustrating an exemplary configuration of an ultrasonic diagnosis apparatus according to a fifth embodiment of the present invention.
Figure 9:
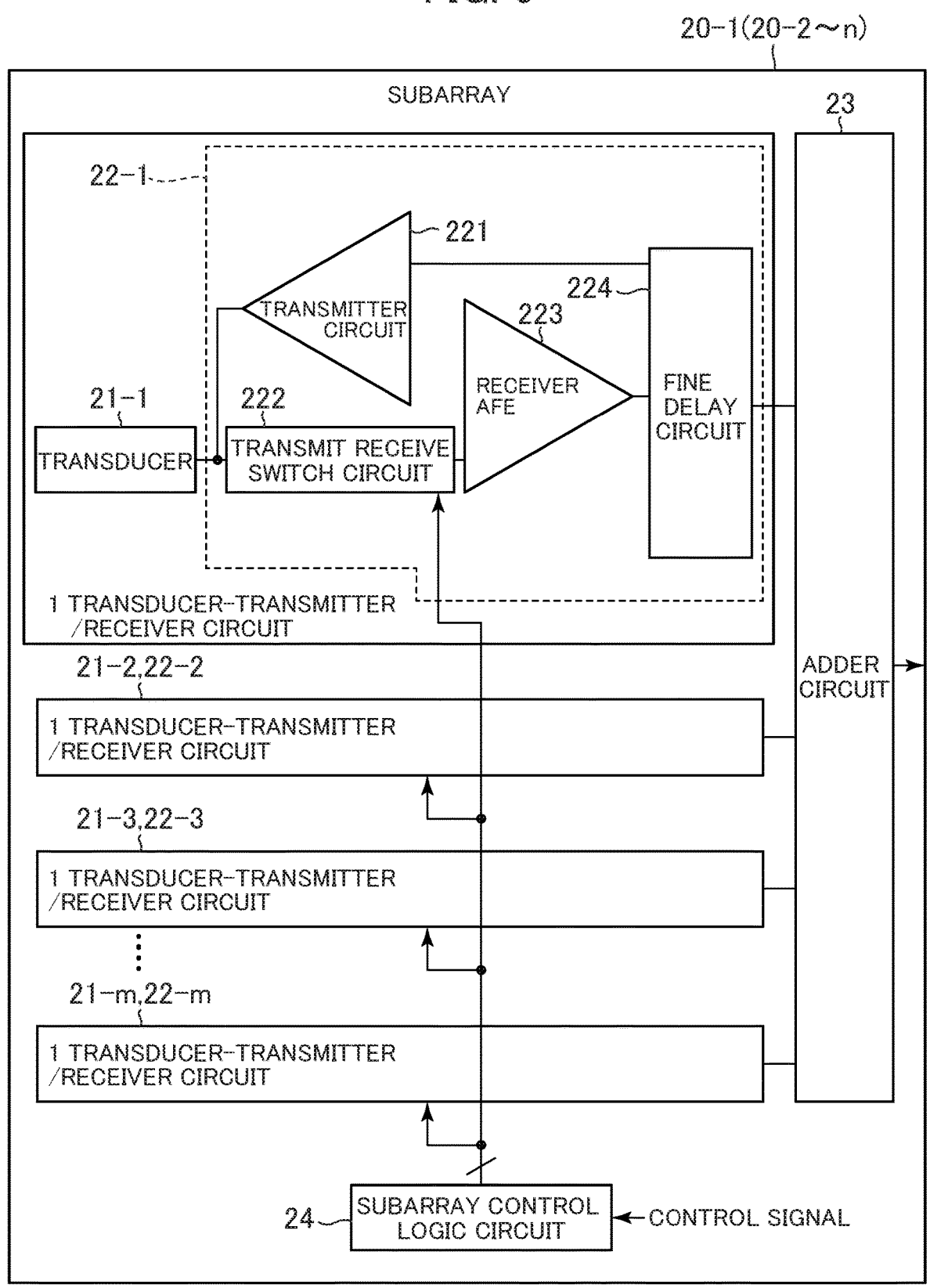
FIG. 9 is a block diagram illustrating an exemplary configuration of a subarray in the ultrasonic diagnosis apparatus depicted in FIG. 8.

Referring now to FIGS. 8 and 9, an ultrasound probe using the transmit receive switch circuit and an ultrasonic diagnosis apparatus will be described in accordance with a fifth embodiment of the present invention. FIG. 8 is a block diagram illustrating an exemplary configuration of the ultrasonic diagnosis apparatus according to the fifth embodiment. FIG. 9 is a block diagram illustrating an exemplary configuration of a subarray. The fifth embodiment relates to an example of the ultrasound probe that uses the transmit receive switch circuit described in conjunction with the first to fourth embodiments, and also relates to an example of the ultrasonic diagnosis apparatus that uses the ultrasound probe.

The ultrasonic diagnosis apparatus transmits ultrasonic waves into a test object by supplying a high-voltage drive signal to each of multiple transducers built in the ultrasound probe. The multiple transducers respectively receive reflections of the ultrasonic waves, which are generated in accordance with acoustic impedance difference between body tissues in the test object. Based on the reflections of the ultrasonic waves, which are received by the ultrasound probe, the ultrasonic diagnosis apparatus generates an image.

In recent years, an ultrasonic diagnosis apparatus capable of generating a three-dimensional image has been developed. Therefore, increased test efficiency can be achieved when a tomographic image is acquired by designating an arbitrary cross-section of the three-dimensional image. For three-dimensional imaging, the array of transducers in an ultrasound probe needs to be changed from a conventional one-dimensional array to a two-dimensional array. Thus, the number of transducers increases by the square of the conventional number of transducers. In this instance, the number of cables connecting the ultrasound probe to a main unit of the apparatus cannot be increased by the square. Therefore, signals received after the number of cables is decreased by phasing addition in the ultrasound probe need to be transferred to the main unit of the apparatus through the cables.

FIG. 8 illustrates a configuration of the ultrasonic diagnosis apparatus that is formed of a main unit 50 and an ultrasound probe 10 having two-dimensionally arrayed transducers. The ultrasound probe 10 includes multiple subarrays 20 (20-1 to 20-n; n pieces) and an IC control logic circuit 30. The subarrays 20 each include multiple transducers 21 (21-1 to 21-m; m pieces), multiple transmitter/receiver circuits 22 (22-1 to 22-m) for the transducers 21, an adder circuit 23 common to the transmitter/receiver circuits 22, and a subarray control logic circuit 24 for controlling the transmitter/receiver circuits 22. In the ultrasound probe 10, the transmitter/receiver circuits 22, the adder circuit 23, and the subarray control logic circuit 24 are formed of an integrated circuit (IC). The integrated circuit and the transducer 21 associated with the integrated circuit are superimposed one over the other in a one-to-one dimension.

The main unit 50 includes AFEs (analog front-ends) 51 (51-1 to 51-n) and a processor 52. The AFEs 51 are associated with the subarrays 20 of the ultrasound probe 10. The processor 52 controls the IC control logic circuit 30 of the ultrasound probe 10. The main unit 50 not only controls the ultrasound probe 10 but also performs image processing.

The ultrasonic diagnosis apparatus according to the fifth embodiment is configured so that the transmitter/receiver circuits 22 are disposed for the transducers 21 within the ultrasound probe 10, and that reception outputs from the transmitter/receiver circuits 22 are added by the adder circuit 23 addition and forwarded to an AFE (51) in the main unit 50. A grouping unit of transducer channels to be added by the adder circuit 23 is called a subarray 20.

The processor 52 in the main unit 50 transmits a control signal to the IC control logic circuit 30 in the ultrasound probe 10. Upon receipt of the control signal from the processor 52, the IC control logic circuit 30 exercises control, such as transmission/reception switching control, in accordance with the control signal. As regards transmission/reception switching for controlling the transmit receive switch circuit, the subarrays 20 can be collectively controlled to reduce the scale of the IC control logic circuit 30 or the number of control signal lines in the IC. Alternatively, as indicated in FIG. 8, the subarray control logic circuit 24 can be disposed for each subarray 20 to formulate a hierarchical control scheme and let the subarray control logic circuit 24 exercise minute control over the transmitter/receiver circuits 22 on an independent basis.

FIG. 9 illustrates an internal configuration of the subarray 20-1 (the same holds true for the subarrays 20-2 to 20-n). The transmitter/receiver circuit 22-1 (the same holds true for the transmitter/receiver circuit 22-2 to 22-m) for each transducer includes a transmitter circuit 221, a transmit receive switch circuit 222, a receiver AFE (223), and a fine delay circuit 224. The transmitter circuit 221 is formed of a high-voltage MOSFET and generates a high-voltage to drive the transducer 21-1. The transmit receive switch circuit 222 is the switch circuit described in conjunction with the first to fourth embodiments. The receiver AFE (223) is a low-voltage receiver analog front-end. The fine delay circuit 224 delays a transmit signal to perform beamforming and delays a received signal to perform phasing.

The received signals phased by the fine delay circuits 224 are added by the adder circuit 23 and transferred to the main unit 50. Referring to FIG. 9, a signal from the subarray control logic circuit 24 exercises on-off control over the transmit receive switch circuit 222 on an individual transducer channel basis.

The ultrasound probe 10 using the transmit receive switch circuit, and the ultrasonic diagnosis apparatus, which are described in conjunction with the fifth embodiment, provides the following advantageous effects because the advantageous effects of the transmit receive switch circuit described in conjunction with the first to fourth embodiment are obtained.

For example, the area of the integrated circuits in the ultrasound probe 10 can be reduced. Further, when the circuit area is reduced, a grating lobe caused by diffraction can be reduced by decreasing the intervals at which the transducers 21 are arranged. As a result, the image quality of the ultrasonic diagnosis apparatus can be improved. Moreover, the power consumption can be decreased to reduce the heat generated by the ultrasound probe 10. Consequently, the ultrasound probe 10 can be naturally air-cooled and implemented at a low cost.

The first to fifth embodiments, which have been described above, provide the advantageous effects when implemented in the integrated circuits in the ultrasound probe 10 connected to the ultrasonic diagnosis apparatus. When the embodiments are used, the transmit receive switch circuit using only three high-voltage MOSFETs can be implemented. Further, the embodiments use the shunt circuit in which no steady-state current flows, and enable the shunt circuit to automatically assure the switch-off state at the time of negative-voltage wave transmission. Moreover, the time constant with which the shunt circuit reacts can be arbitrarily set as appropriate for the frequency of an outgoing high-voltage signal by properly selecting a resistance value and a capacitance value. That is to say, the embodiments provide an advantageous technology for separating a low-voltage circuit from a high-voltage signal and allowing a weak signal to pass while achieving small area and low power consumption.

While the present invention made by its inventors has been described in detail with reference to the embodiments, the present invention is not limited to the foregoing embodiments. It is to be understood by those skilled in the art that various modifications can be made without departing from the spirit and scope of the present invention.

LIST OF REFERENCE SIGNS

MN1 to MN4 . . . NMOSFET
MP1 . . . PMOSFET
C1 . . . Capacitor
R1 . . . Resistor
D1 to D2 . . . Diode
INV1 to INV2 . . . Logic inverter
SHNT . . . Shunt circuit
Vdd . . . Supply voltage
COMG . . . Common gate
COMS . . . Common source
SWIN . . . Switch input
SWOUT . . . Switch output

The invention claimed is:

1. A switch circuit that has a first MOSFET and a second MOSFET, and goes into a switch-off state at the time of transmission and goes into a switch-on state at the time of reception, the first MOSFET and the second MOSFET being connected between an input terminal and an output terminal, the switch circuit comprising:
a shunt circuit that is connected between a common gate and a common source, the common gate being connected to gates of the first MOSFET and the second MOSFET, the common source being connected to sources of the first MOSFET and the second MOSFET,
wherein, when a signal having a negative voltage relative to a reference voltage is applied to the input terminal, a switch that temporarily turns on causes the shunt circuit to short-circuit the common gate and the common source, and
wherein the shunt circuit includes:
a filter that is connected between the common gate and the common source and formed of a resistor and a capacitor; and
a third MOSFET that is connected to the filter and is used as the switch.

2. The switch circuit according to claim 1,
wherein the third MOSFET of the shunt circuit short-circuits the common gate and the common source when the voltage between the common gate and the common source increases with a time constant not greater than a time constant equal to the product of the resistance value of the resistor and the capacitance value of the capacitor; and
wherein the time constant equal to the product of the resistance value of the resistor and the capacitance value of the capacitor is adjustable.

3. The switch circuit according to claim 2,
wherein the first MOSFET and the second MOSFET have a higher withstanding voltage than the third MOSFET.

4. The switch circuit according to claim 3, further comprising:
a resistor that is connected between the common gate and the common source and in parallel with the shunt circuit in order to maintain the switch-off state by avoiding the floating of the common gate as viewed from the common source in the switch-off state.

5. The switch circuit according to claim 3, further comprising:
diodes that are connected to the output terminal in order to clamp high-potential side and low-potential side with respect to the reference voltage of a signal applied to the input terminal in the switch-on state.

6. The switch circuit according to claim 3, further comprising:
a fourth MOSFET that is connected to the output terminal in order to short-circuit the output terminal with respect to the reference voltage of a signal applied to the input terminal in the switch-on state;
wherein the fourth MOSFET has a lower withstanding voltage than the first MOSFET and the second MOSFET.

7. The switch circuit according to claim 3, further comprising:
a fifth MOSFET that is connected to the common gate in order to invoke, when turned on, the switch-on state by applying a predetermined supply voltage to the common gate, and invoke, when turned off, the switch-off state by setting the voltage between the common gate and the common source to a voltage not higher than a threshold voltage;
wherein the fifth MOSFET has a higher withstanding voltage than the third MOSFET.

8. The switch circuit according to claim 7,
wherein the fifth MOSFET is controlled by a logical high or logical low control signal having a voltage lower than the withstanding voltage of the fifth MOSFET.

9. The switch circuit according to claim 8,
wherein a source of the fifth MOSFET is controlled by a logical high or logical low control signal having a voltage lower than the withstanding voltage of the fifth MOSFET; and
wherein, when a transition is made between the switch-on state and the switch-off state, a logic circuit driving the control signal supplies a charge/discharge current for the common gate through the fifth MOSFET.

10. An ultrasound probe using the switch circuit according to claim 1, the ultrasound probe comprising:
a transmitter circuit that transmits a signal having a first voltage to drive a transducer;
a receiver circuit that receives a signal having a second voltage from the transducer, the second voltage being lower than the first voltage; and
the switch circuit that goes into the switch-off state at the time of transmission in order to isolate the receiver circuit from a signal transmitted from the transmitter circuit, and goes into the switch-on state at the time of reception in order to allow a signal from the transducer to pass to the receiver circuit.

11. The ultrasound probe according to claim 10, comprising:
a plurality of units of the transmitter circuit;
a plurality of units of the receiver circuit;
a plurality of units of the switch circuit; and
an adder circuit that adds signals from the plurality of units of the receiver circuit.

12. The ultrasound probe according to claim 11,
wherein the plurality of units of the transmitter circuit, the plurality of units of the receiver circuit, the plurality of units of the switch circuit, and the adder circuit form a subarray; and
wherein a plurality of units of the subarray are included in the ultrasound probe.

13. The ultrasound probe according to claim 12,
wherein the plurality of units of the transmitter circuit, the plurality of units of the receiver circuit, the plurality of units of the switch circuit, and the adder circuit, which are included in the plurality of units of the subarray, are formed of an integrated circuit; and
wherein the integrated circuit is superimposed over two-dimensionally arrayed units of the transducer.

14. An ultrasonic diagnosis apparatus using the ultrasound probe according to claim 10, the ultrasonic diagnosis apparatus comprising:
the ultrasound probe; and
a main unit that not only controls the ultrasound probe but also performs image processing.

* * * * *